US009279746B2

(12) United States Patent
Wynn

(10) Patent No.: US 9,279,746 B2
(45) Date of Patent: Mar. 8, 2016

(54) INLINE OPTICAL SENSOR WITH MODULAR FLOWCELL

(75) Inventor: William H. Wynn, Hillsborough, CA (US)

(73) Assignee: Endress+ Hauser Conducta Inc., Anaheim, CA (US)

( * ) Notice: Subject to any disclaimer, the term of this patent is extended or adjusted under 35 U.S.C. 154(b) by 983 days.

(21) Appl. No.: 13/398,084

(22) Filed: Feb. 16, 2012

(65) Prior Publication Data
US 2013/0215412 A1    Aug. 22, 2013

(51) Int. Cl.
| G01N 1/10  | (2006.01) |
| G01N 21/05 | (2006.01) |
| G01N 21/03 | (2006.01) |

(52) U.S. Cl.
CPC .............. *G01N 1/10* (2013.01); *G01N 21/0303* (2013.01); *G01N 21/05* (2013.01); *G01N 2021/0307* (2013.01)

(58) Field of Classification Search
CPC ........ G01N 30/04; G01N 30/10; G01N 30/12
USPC ......... 356/436–445, 128, 244–246, 338, 319; 250/458.1, 576, 343, 910
See application file for complete search history.

(56) References Cited

U.S. PATENT DOCUMENTS

| 3,773,424 | A |   | 11/1973 | Selgin |
| 5,223,716 | A |   | 6/1993  | Rossiter |
| 5,905,271 | A | * | 5/1999  | Wynn ............................ 356/436 |
| 6,512,223 | B1|   | 1/2003  | Wynn |
| 6,857,638 | B2|   | 2/2005  | Dupont et al. |
| 7,369,226 | B1| * | 5/2008  | Hewitt ............... G01N 21/0303 356/244 |
| 7,973,923 | B2|   | 7/2011  | Wynn et al. |
| 8,049,884 | B2| * | 11/2011 | Tsukuda .............. G01N 21/251 356/319 |
| 2008/0252881 | A1 |   | 10/2008 | Yakimoski et al. |
| 2011/0048964 | A1 | * | 3/2011  | Luebke et al. ................ 205/687 |
| 2012/0061579 | A1 |   | 3/2012  | Wynn |
| 2012/0119101 | A1 |   | 5/2012  | Wynn |

FOREIGN PATENT DOCUMENTS

| CN | 85200040 U   | 12/1985 |
| CN | 101105441 A  | 1/2008  |

(Continued)

OTHER PUBLICATIONS

Ministry of Chemical Industry of the People's Republic of China, "GB10708.3-89 Reciprocating rubber seals—Design Criteria for standard applications—Part 3: rubber seals for wipers", PRC National Standard (1989).

(Continued)

*Primary Examiner* — Tarifur Chowdhury
*Assistant Examiner* — Iyabo S Alli
(74) *Attorney, Agent, or Firm* — Edward S. Wright

(57) ABSTRACT

Inline optical sensor which includes a modular flowcell block with a flow passageway of predetermined diameter, interchangeable adapters for connecting flow lines with different internal diameters to the block, and an optical pathlength that can be adjusted both in fixed increments with window spacers and continuously with vernier adjusters, and a light source and an optical detector in modular housings which can be aligned both radially and axially. Thermal isolation is provided between the housings and the flowcell body, and air circulation further reduces temperature and condensation within the housings.

38 Claims, 7 Drawing Sheets

(56) References Cited

FOREIGN PATENT DOCUMENTS

| | | |
|---|---|---|
| CN | 101143270 A | 3/2008 |
| CN | 101285760 A | 10/2008 |
| CN | 102072880 A | 5/2011 |
| CN | 201886013 U | 6/2011 |
| CN | 202094051 U | 12/2011 |
| CN | 102353631 A | 2/2012 |
| EP | 0335268 A2 | 10/1989 |
| EP | 0414032 A1 | 2/1991 |
| GB | 1453602 A | 10/1976 |

OTHER PUBLICATIONS

Song, Xueyi, "Pocket Hydraulics and Pneumatics Handbook", pp. 1834 (1995).

* cited by examiner

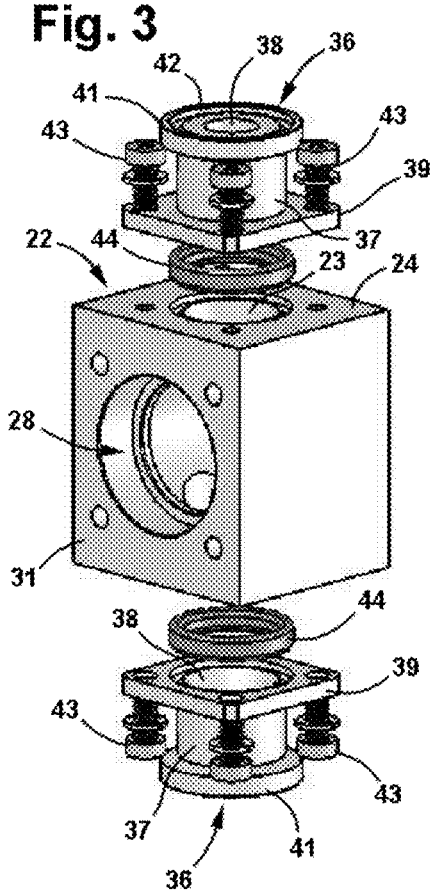
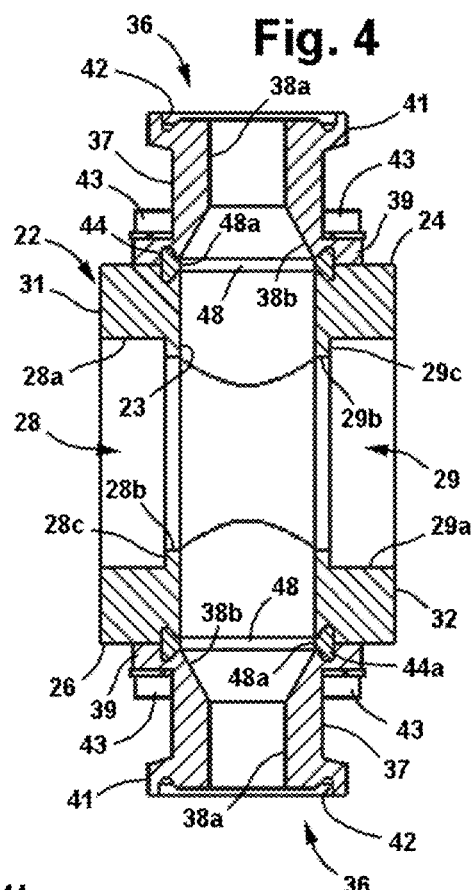
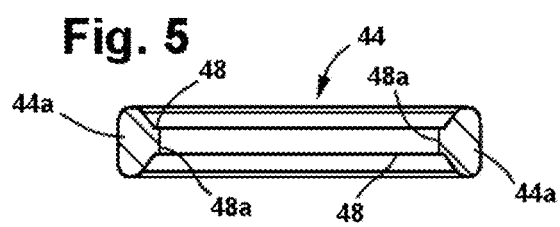
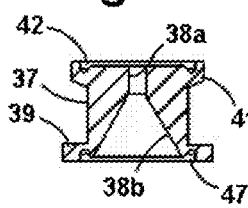
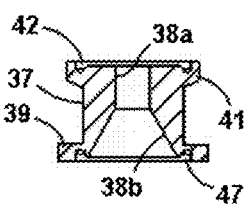
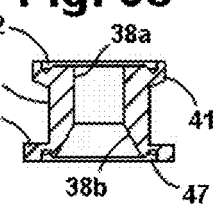
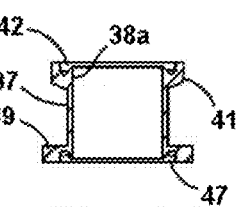

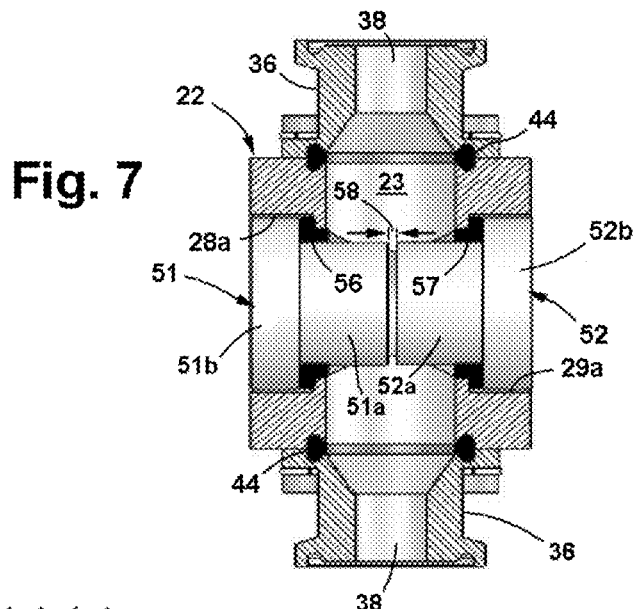
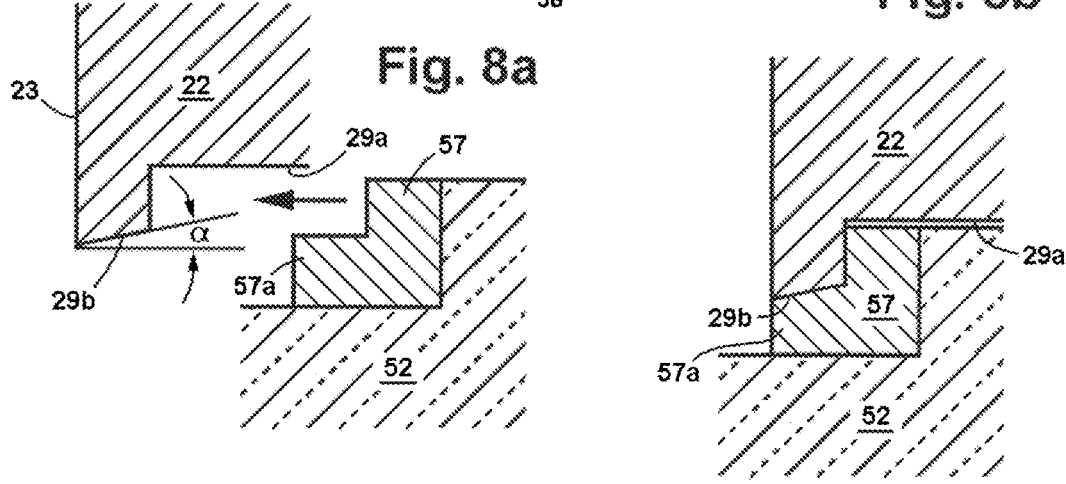
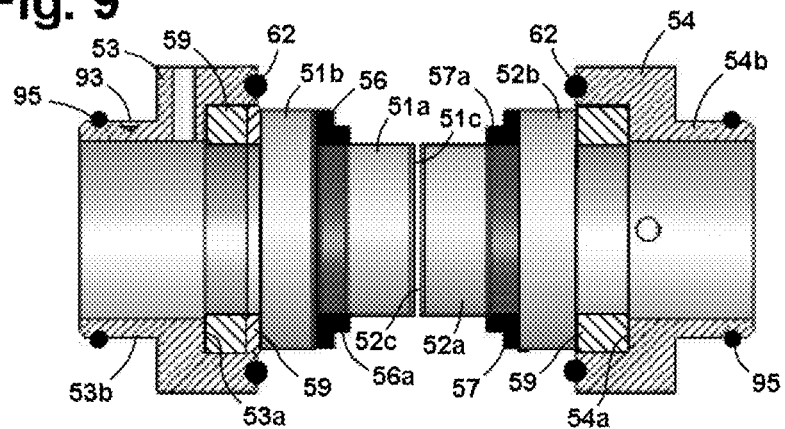

Fig. 10
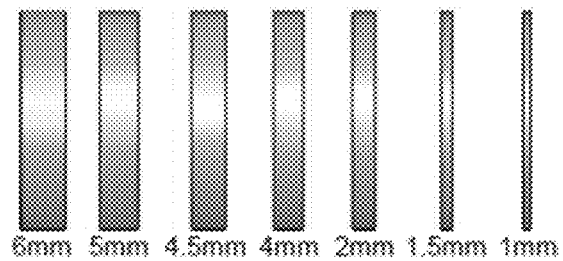
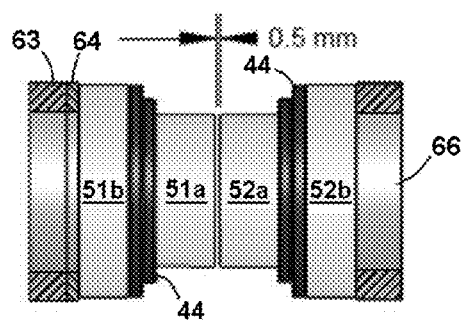
Fig. 11a
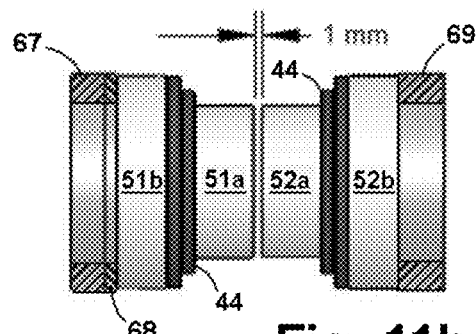
Fig. 11b
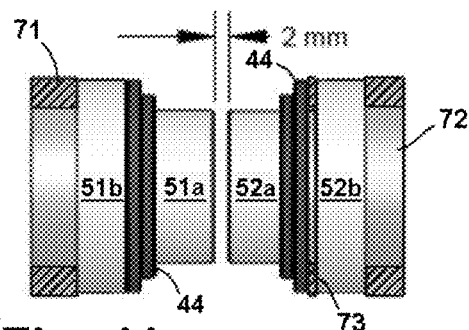
Fig. 11c
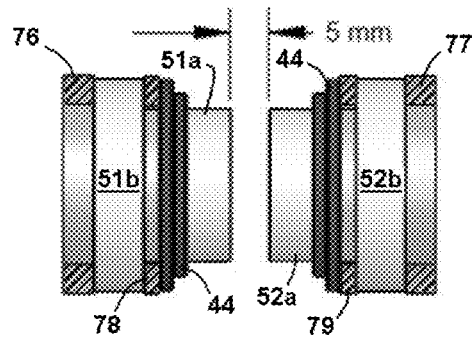
Fig. 11d
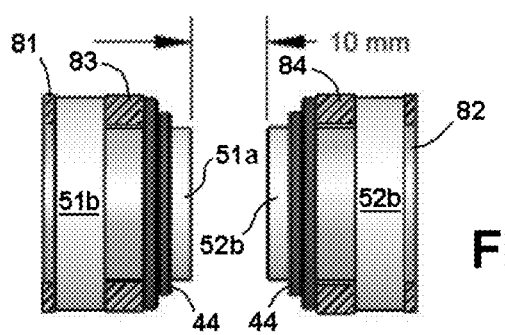
Fig. 11e

INLINE OPTICAL SENSOR WITH MODULAR FLOWCELL

BACKGROUND OF THE INVENTION

1. Field of Invention

This invention pertains generally to inline optical sensors and, more particularly, to an inline optical sensors having a modular flowcell that can accommodate different line sizes and different optical pathlengths.

2. Related Art

Flowcells are used widely in inline optical sensors for monitoring the properties of product streams in the biotechnology field and in other sanitary applications. The flow lines employed in such applications typically have internal diameters ranging in size from ⅛ inch to ¾ inch (approximately 3 mm to 19 mm), and heretofore it has been necessary to manufacture flowcells with passageways corresponding to the different line sizes. With passageways of smaller diameters, proper drainage can be a problem even if the flowcell is mounted with the passageway extending vertically.

Such instruments typically have optical windows positioned on opposite sides of the product stream, with a light source outside one of the windows for directing a beam through the stream and a detector outside the other for receiving the beam. The light can be in the ultra violet, visible or near infrared spectrums. The length of the optical path through the fluid stream is determined by the spacing between the windows, and heretofore the only way to change the pathlength significantly has been to use windows of different lengths. That requires a different pair of windows for every pathlength, and varying an optical pathlength from 0.5 mm to 20 mm could, for example, require as many as seven sets of windows. Moreover, the O-ring gaskets typically utilized in sealing such windows can be difficult to sanitize with commonly used clean-in-place (CIP) and steam-in-place (SIP) cleaning procedures.

Another problem with optical sensor flowcells is alignment of the light source and detector along the optical axis. While some existing flowcells may permit proper axial alignment, radial alignment is generally not possible.

OBJECTS AND SUMMARY OF THE INVENTION

It is, in general, an object of the invention to provide a new and improved inline optical sensor and flowcell.

Another object of the invention is to provide an inline optical sensor and flowcell of the above character which overcomes limitations and disadvantages of inline sensors and flowcells heretofore provided.

These and other objects are achieved in accordance with the invention by providing an inline optical sensor having a flowcell block, a flow passageway of predetermined diameter extending through the block, a plurality of adapters for connecting product lines with different internal diameters to the flowcell, each of the adapters having a bore that matches the diameter of the flow passageway at one end and the internal diameter of one of the product lines at the other, means for interchangeably attaching the adapters to the block at opposite ends of the flow passageway, monitoring ports which intersect the flow passageway and open through opposite sides of the block, optical windows disposed in the ports, a light source and an optical detector aligned with each other on an optical axis that passes through the passageway and the windows, and a plurality of spacers interchangeably positioned on opposite sides of one of the windows for establishing different optical pathlengths between the windows.

BRIEF DESCRIPTION OF THE DRAWINGS

FIG. 3 is an exploded isometric view of the flowcell block and product line adapters in the embodiment of FIG. 1.

FIG. 4 is a vertical sectional view of the flowcell block and adapters of FIG. 3 in an assembled state.

FIG. 5 is an enlarged sectional view of one of the gaskets that form seals between the flowcell block and the product line adapters in the embodiment of FIG. 1.

FIGS. 6a-6d are vertical sectional views of additional product line adapters for use in the embodiment of FIG. 1.

FIG. 7 is a vertical sectional view of the optical windows and flowcell block in the embodiment of FIG. 1, taken in a direction perpendicular to the optical axis.

FIG. 8a is an enlarged, exploded, fragmentary, sectional view of the window seal and seat in the embodiment of FIG. 7.

FIG. 8b is a view similar to FIG. 8a, showing the window seal in its seated position in the flowcell block.

FIG. 9 is a vertical sectional view of the window mounting rings and windows in the embodiment of FIG. 1.

FIG. 10 is a side elevational view of a set of window spacers for use in the embodiment of FIG. 1.

FIGS. 11a-11e are centerline sectional views of a pair of windows with different combinations of spacers providing different optical pathlengths between the windows.

DETAILED DESCRIPTION

Figure 1:
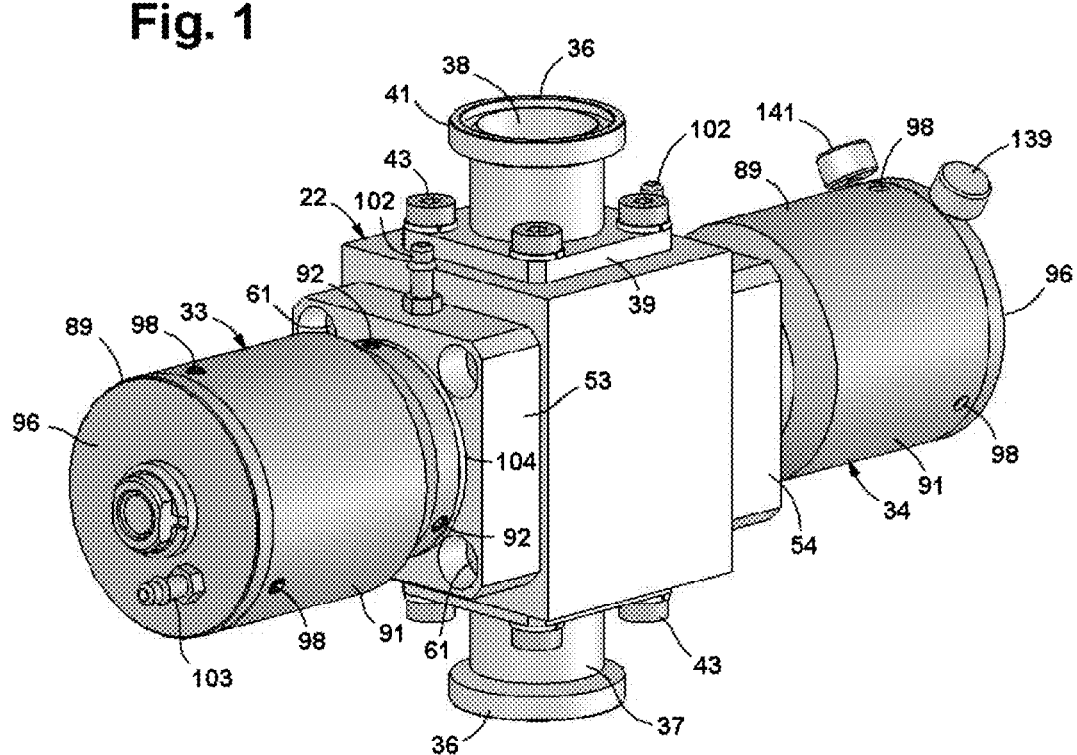
FIG. 1 is an isometric view of one embodiment of an optical sensor with a modular flowcell according to the invention.

The inline optical sensor includes a stainless steel flowcell block or body 22 with a flow passageway 23 opening through the upper and lower sides 24, 26 of the block. Monitoring ports 28, 29 open through opposite sides 31, 32 of the block and intersect the passageway at right angles. A light source 33 and detector 34 are mounted on the block in alignment with the ports, with light from the source passing through the passageway to the detector. Both the passageway and the ports are circular in cross section.

Product lines (not shown) are connected to the flowcell block by adapters 36 having a cylindrical body 37 with an internal bore 38, a mounting flange 39 at one end of the body, and a fitting 41 for connection to the product line at the other. The fittings illustrated are Tri-Clover® connectors with seal grooves 42 in the outer faces of the fittings, but any suitable connectors can be utilized, including VCR® fittings, tubing connectors, hose barbs, and the like. The adapters are secured to the block by mounting screws 43.

Sealing between the flowcell block and the line adapters is provided by sanitary tube fitting gaskets 44 which have generally toroidal bodies 44a that are received in matching grooves 46, 47 in the confronting surfaces of the flowcell block and the mounting flanges. These gaskets have relatively short annular flanges 48 that extend inwardly from the generally toroidal bodies, with the inner faces 48a of the flanges aligned with the side walls of the passageway in the block and the bores in the adapters.

The gaskets are under controlled compression, with the inner faces 48a accurately aligned with the walls of the passageway and the bores when the mounting screws are tightened to bring the surfaces of the mounting flanges and the block together in firm contact. The controlled compression provides tight seals and ensures that the integrity of the seals will be maintained, even during repeated CIP and SIP cycles. This type of gasket is a standard component that is used extensively in other applications in the biotech industry and is available in various materials, including some meeting the requirements for FDA Class VI certification.

With the adapters, a standardized flowcell of predetermined passageway diameter can be utilized with product lines of different internal diameters. Thus, for example, in the embodiment shown in FIG. 4, the passageway has a larger diameter than the product line, and the adapter bore has a cylindrical section 38a at the connector end with a diameter equal to the internal diameter of the product line. A conically tapered section 38b extends between the inner end of the cylindrical section and the outer surface of the mounting flange, with a diameter that increases from the diameter of the product line to the diameter of the passageway. This taper provides a smooth transition between the different diameters and allows the sensor to be up to 60 degrees from vertical and still have proper draining, even with lines as small as ⅛ inch or less. The adapters allow the passageway in the flowcell to be larger and produce a lower drop in pressure than flowcells with smaller passageways.

Adapters for use with product lines of different internal diameters are shown in FIGS. 6a-6d. With a flowcell having a passageway diameter of ¾ inch, for example, the cylindrical bores 38a in the adapters shown might have diameters of ⅛ inch, ¼ inch, ½ inch, and ¾ inch, respectively. From these examples, it will be noted that the cone angle is the same in all of the adapters but the length of the tapered section 38b decreases as the diameter of the line and the cylindrical section increases, reaching zero when the diameter of the line is the same as the diameter of the passageway. Regardless of the bore size, however, the outer dimensions of the adapter and manner in which it is connected to the product line and the flowcell block remain the same.

Changing from one line size to another is simply a matter of removing the existing adapters from the flowcell block, replacing the gaskets in the block, and mounting the new adapters on the block. When the mounting screws have been tightened and the surfaces of the mounting flanges and the flowcell block are together, the controlled compression provided thereby ensures proper sealing with the new gaskets.

Optically transparent windows 51, 52 are mounted in monitoring ports 28, 29 and retained in position by mounting rings 53, 54, respectively. As best seen in FIG. 4, each of the monitoring ports has an outer section of relatively large diameter with a cylindrical side wall 28a, 29a, an inner section of lesser diameter with a conically tapered side wall 28b, 29b that opens into flow passageway 23, and an outwardly facing annular shoulder 28c, 29c between the side walls of the two sections.

The windows have solid cylindrical bodies 51a, 52a, with radial flanges 51b, 52b toward the outer ends thereof. In the embodiment illustrated, the thickness of the flanges is approximately one-third of the length of the bodies. Thus, for example, in a window having a length of 18 mm, the flange might have a thickness of about 6 mm. The diameter of the flanges is somewhat less than that of the outer sections of the monitoring ports.

Stepped O-ring gaskets 56, 57 provide liquid-tight seals between the windows and the flowcell block. These gaskets have generally annular bodies with a step 56a, 57a of reduced outer diameter on one side thereof. The gaskets are fabricated of a resilient material such as rubber and have an inner diameter slightly less (e.g., 1-2 percent) than the diameter of the windows. The elasticity of the gasket urges the inner surface of the gasket tightly against the side wall of the window body, forming the primary seal between the window and the gasket. A secondary seal is formed between the confronting faces of the gasket and the window flange. The flat face contact with the window flange reduces the strain on the window by spreading the sealing force applied to the window over a wider area than that a conventional O-ring seal The stepped portions of the gaskets face inwardly toward the flow passageway and are received in the seats formed by the conically tapered side walls 28b, 29b of the inner sections of the monitoring ports. As illustrated in somewhat exaggerated form in FIGS. 8a and 8b, the walls that form the seats are inclined at an angle α which can, for example, be on the order of 6 degrees. When the step portions of the gaskets are pressed into the seats, the step portions are compressed between the seats and the side walls of the window bodies, creating an even tighter seal with the windows. Having the primary seals between the side walls of the windows and the inner surfaces of the gaskets makes it possible to use spacers between the window flanges and the gaskets to vary the length of the pathway or spacing 58 between the inner faces of the windows.

The entrance diameter of the sensor windows is such that the liquid faces of the stepped O-ring gasket are fully exposed. This exposure ensures that all surfaces in contact with the liquid are sterilized during CIP and SIP cleaning procedures.

The bodies of the windows extend into the flow passageway, and the length of the optical path between inner faces 51c, 52c is determined by spacers 59 which can be selectively positioned on opposite sides of the window flanges. Thus, for example, in the embodiment illustrated in FIG. 9, two spacers 59, 59 are positioned on the outer side of the window flange 51b, and a single spacer 59 is positioned on the outer side of window flange 52b. In this particular example, the total thickness or width of the two spacers outside flange 51b is equal to the thickness or width of the single spacer outside flange 52b, and the two windows extend equal distances into the passageway.

The spacers have annular bodies with an inner diameter slightly greater than the bodies of the windows and an outer diameter slightly greater than the outer diameters of the window flanges and the stepped O-ring gaskets. In one presently preferred embodiment, the spacers are fabricated of a thermoplastic material such as polyether ether ketone (PEEK).

The window mounting rings have recessed areas or cavities 53a, 54a in which the window flanges and spacers on the outer sides of the flanges are received. The recesses are circular and have a diameter slightly greater than the spacers.

The mounting rings are secured to the sides of the flowcell block by mounting screws 61, with O-rings 62 providing liquid-tight seals between the mounting rings and the side faces of the block.

FIG. 10 illustrates a set of spacers which can be used individually or in combination to provide the desired pathlength. In this example, the set includes spacers having widths of 1 mm, 1.5 mm, 2 mm, 4 mm, 4.5 mm, 5 mm, and 6 mm, and FIGS. 11a-11e illustrate the use of such spacers to provide pathlengths ranging from 0.5 mm to 10.0 mm with a single pair of windows 51, 52 having a predetermined fixed length of 18 mm.

In the example of FIG. 11a, a 5 mm spacer 63 and a 1.5 mm spacer 64 are placed on the outer side of flange 51b, a 6 mm spacer 66 is placed on the outer side of flange 52b, and the pathlength between the inner faces of the windows is 0.5 mm.

In the example of FIG. 11b, a 4.5 mm spacer 67 and a 1.5 mm spacer 68 are placed on the outer side of flange 51b, a 6 mm spacer 69 is placed on the outer side of flange 52b, and the pathlength between the inner faces of the windows is 1.0 mm.

In the example of FIG. 11c, 4 mm spacers 71, 72 are placed on the outer sides of flanges 51b, 52b, 2 mm spacers 73, 74 are positioned between the inner faces of flanges 51b, 52b and the outer faces of stepped gaskets 56, 57, and the pathlength between the inner faces of the windows is 5.0 mm.

In the example of FIG. 11d, 1.5 mm spacers 76, 77 are placed on the outer sides of flanges 51b, 52b, 2 mm spacers 78, 79 are positioned between the inner faces of flanges 51b, 52b and the outer faces of stepped gaskets 56, 57, and the pathlength between the inner faces of the windows is 5.0 mm.

In the example of FIG. 11e, 1.5 mm spacers 81, 82 are placed on the outer sides of flanges 51b, 52b, 5 mm spacers 83, 84 are positioned between the inner faces of flanges 51b, 52b and the outer faces of stepped gaskets 56, 57, and the pathlength between the inner faces of the windows is 10.0 mm.

Figure 12:
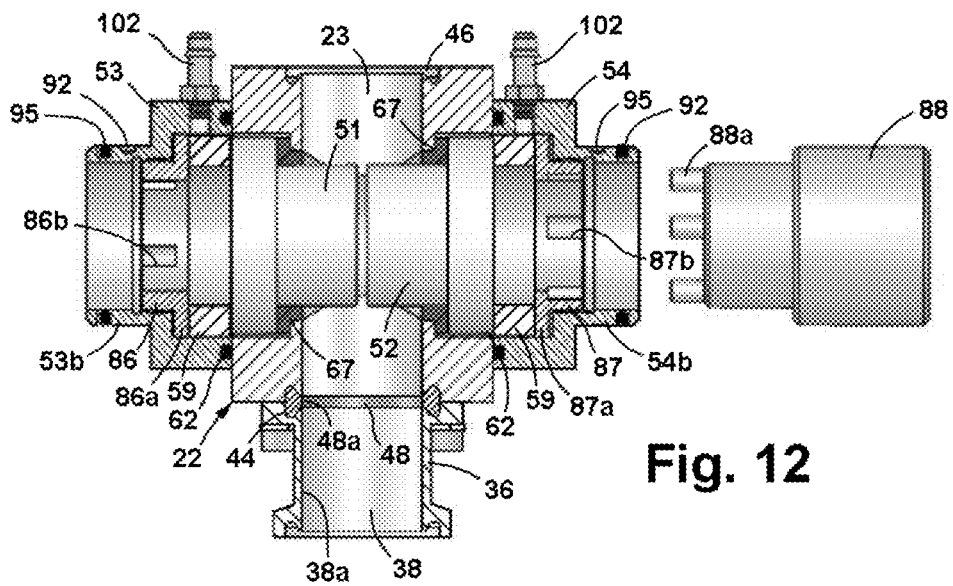
FIG. 12 is a centerline sectional view, illustrating the vernier window adjusters in the embodiment of FIG. 1.

The window mounting rings have vernier adjusters for finer adjustment of the pathlength between the window faces than that provided by the spacers. These adjusters can also be utilized to correct for mechanical tolerances that affect the window spacing. As best seen in FIG. 12, each of the window mounts has an axially extending barrel 53b, 54b in which an adjusting collar 86, 87 is threadedly mounted for movement toward and away from the flow passageway. The collar has a radial flange 86a, 87a at its inner end which engages the outer faces of the window flanges and the spacers. The collars are rotated with an adjusting key 88 with drive pins 88a that engage the walls of sockets 86b, 87b in the collars. When the collars are turned in one direction they travel in an inward direction, compressing the stepped O-ring gaskets to decrease the distance between the windows and shorten the pathlength. When the collars are turned in the opposite direction, they travel in an outward direction, allowing the compressed gasket to expand and move the windows apart, thereby increasing the pathlength. The adjustments are preferably made on both windows, with each one being moved a similar distance to achieve the desired pathlength and maintain the integrity of the seals. The window spacing can be measured with feeler or pin gauges inserted into the passageway when one of the line connectors is removed.

The use of vernier adjusters in an inline optical sensor is further discussed in U.S. Pat. No. 5,905,271, the disclosure of which is incorporated herein by reference.

If precise adjustment of the pathlength is not required, the vernier adjusters can be omitted, in which case the pathlength will be determined by the spacers alone. Even without the adjusters, correlation between online and laboratory measurements can be maintained by measuring the window spacing and using the ratio of the desired pathlength to measured spacing as a correction factor for the measured length.

Figure 13:
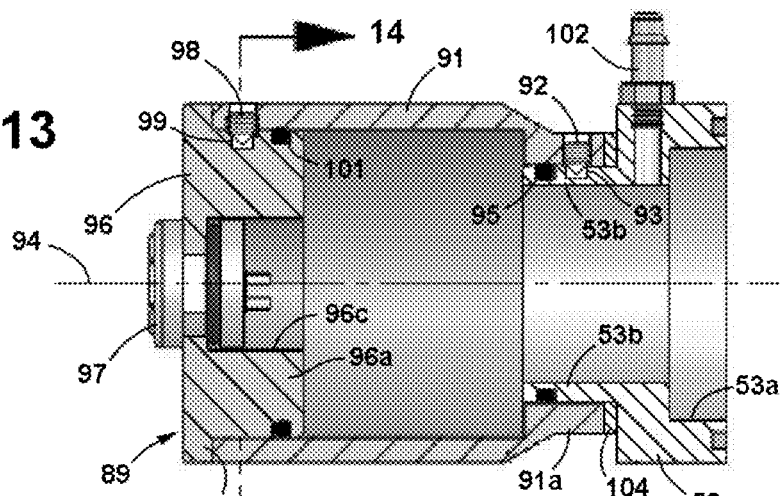
FIG. 13 is a vertical sectional view of one of the housings for the light source and detector in the embodiment of FIG. 1.
Figure 14:
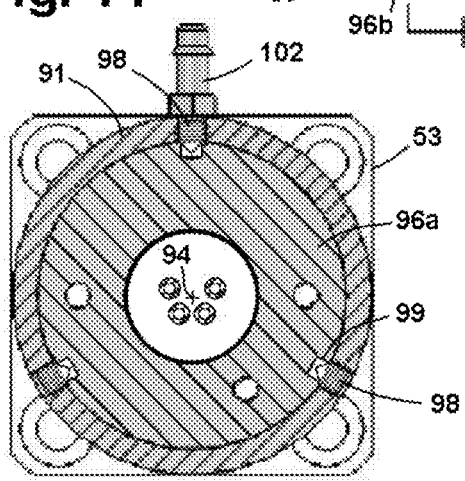
FIG. 14 is a cross sectional view taken along line 14-14 in FIG. 13.
Figure 15:
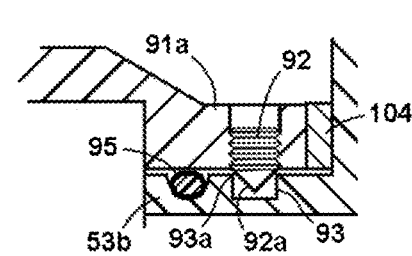
FIG. 15 is an enlarged, fragmentary sectional of a portion of the housing in FIG. 13.

The light source and the detector are enclosed within substantially identical housings 89. As best seen in FIGS. 13-15, housing 89 has a generally cylindrical side wall 91 with a neck portion 91a of reduced diameter which fits over the barrels 53b, 54b of window mounts 53, 54. The housings are affixed to the respective window mounts by conically tapered set screws 92 which are threadedly mounted in the side wall of the housing and received in sockets 93 of smaller diameter than the set screws in the outer wall of the barrel, with the inclined walls 92a of the screws engaging the outer corners 93a of the sockets. The set screws and sockets are spaced 120 degrees apart about optical axis 94 and ensure proper alignment of the light source and detector, both axially and radially. Sealing between the side wall of the housing and the barrel of the window mount is provided by an O-ring 95 which also serves to help maintain the housing wall in concentric alignment with the window mount barrel.

The housing also has an end wall or plug 96 which has a solid cylindrical body 96a which fits within the side wall of the housing and a radial flange 96b which abuts against the outer end of the side wall. A hermetically sealed connector 97 is mounted in a bore 96c in the end wall for making electrical connections to the light source or detector within the housing. The end wall is affixed to the side wall by conically tapered set screws 98 which are threadedly mounted in the side wall and received in sockets 99 of smaller diameter than the set screws in the outer periphery of the end wall body, with the inclined walls of the screws engaging the outer corners 99a of the sockets. These set screws and sockets are also spaced 120 degrees apart and further ensure proper alignment of the light source and detector, both axially and radially. Sealing between the end and side walls of the housing is provided by an O-ring 101.

If desired, the set screws and sockets can be offset from each other along the optical axis to draw the end walls of the housing and the outer faces of the window mounts into tighter engagement with the ends of the side walls of the housings as the screws are tightened.

Means is provided for purging the light source and detector housings with air. This means includes air inlet fittings 102 mounted on the window mounts and air outlet fittings 103 mounted on the end walls of the housings. Air purging can prevent the condensation within the housings in applications where the dew point is such that it might otherwise occur. The air purging is also helpful in preventing damage to or destruction of delicate components in the housing, both during the processing of high temperature products and during SIP sterilization procedures.

Thermal conductivity between the optical modules and the window ring is reduced by an annular ring or gasket 104 of thermally insulative material such as polyether ether ketone (PEEK) between the faces of the window rings and the ends of the housings. Further thermal isolation is provided by the manner in which the modules are attached to the window rings. With the conical set screws and the O-rings between the side walls of the mounting rings and housings, the housings are held concentrically of the window rings with no direct wall-to-wall contact between them. With the only contact between housings and mounts them being through the pointed screws, the O-rings, and insulative gaskets, thermal conductivity between the window rings and the optical modules is significantly less than it would be if the side walls of the rings and modules were in direct contact, and convection heating of the small volume of captive air is the main source of internal heating. Air purging is an efficient and effective method of cooling the optical modules, ensuring that sensitive optical components remain within recommended operating temperature limits even during steam cleaning and with high temperature fluids flowing through the passageway in the flowcell.

Figure 2:
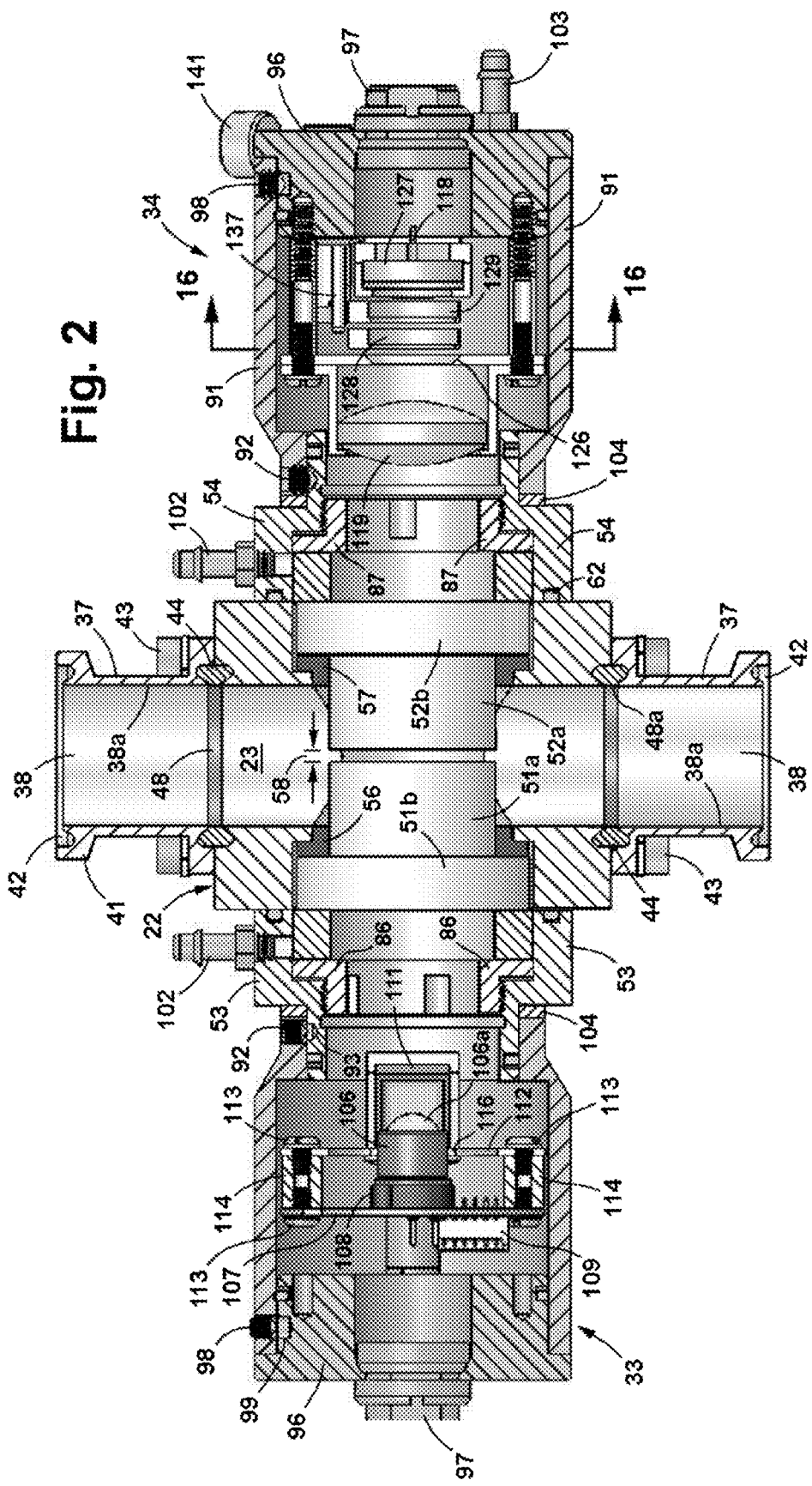
FIG. 2 is a vertical sectional view of the embodiment of FIG. 1.

The light source utilized in the embodiment of FIG. 1 is illustrated in FIG. 2. This source includes a solid state UV emitter or LED (light emitting diode) 106 on a circular printed circuit board 107 mounted to the end wall 96 of the housing by mounting screws and spacers (not shown). The emitter is mounted in a socket 108 on the circuit board along with power control circuitry 109 for the LED. The emitter includes a lens 106a which focuses the emissions from the LED along the optical axis.

A reference detector 111 is mounted on a second circuit board 112 which is attached to the first board by mounting screws 113 and spacers 114, with emitter 106 extending through a central opening 116 in the second board. Spacers 114 are electrically conductive and provide electrical connections between the two boards. The reference detector samples the emitter output, and electrical connections for the reference signal and the power for the emitter are made through connector 97.

Although the light source is illustrated as having a single LED, multiple emitters can be utilized, if desired. Light sources of this type are described in greater detail in application Ser. No. 12/881,438, filed Sep. 14, 2010, the disclosure of which is incorporated herein by reference.

The optical detector utilized in the embodiment of FIG. 1 is also illustrated in FIG. 2. This detector includes a UV silicon detector 118 mounted on the inner side of the end wall 96 of the housing and a quartz objective lens 119 which directs UV light along the optical axis and focuses it on the detector. An aperture 126 and a light blocking filter 127 prevent stray radiation and radiation in the visible spectrum from impinging on the detector.

A pair of calibration filters 128, 129 can be moved into and out of the path between the aperture and the visible light filter. These filters can be either neutral density filters or color filters, depending upon the application for which the sensor is to be used, and in one presently preferred embodiment, they are NIST traceable, i.e. standards whose calibration is part of an unbroken chain of comparison with standards maintained by the National Institute of Standards and Technology. They are calibrated and certified to the measurement wavelength. An optical detector utilizing such filters is described in greater detail in U.S. Pat. No. 6,512,223, the disclosure of which is incorporated herein by reference.

Figure 16:
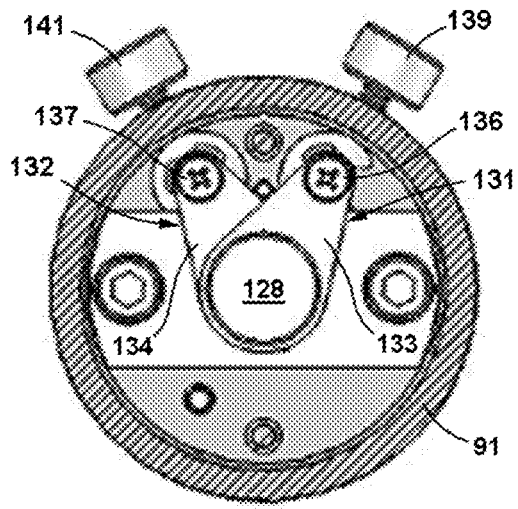
FIG. 16 is a cross sectional view taken along line 16-16 in FIG. 2.
Figure 17:
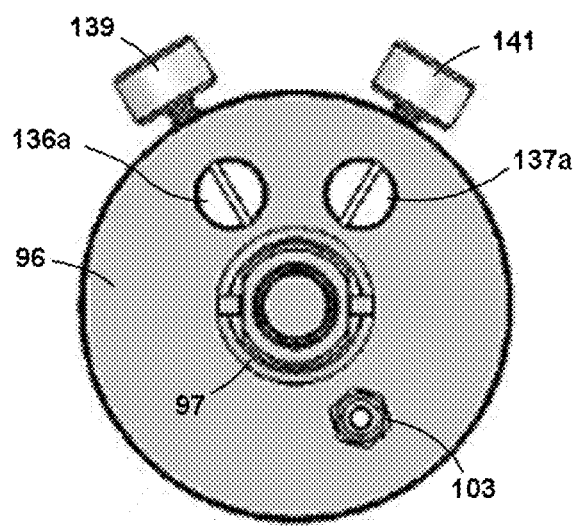
FIG. 17 is an elevational view of the outer end of the detector housing in the embodiment of FIG. 1.

As best seen in FIGS. 16 and 17, the calibration filters are mounted on pivot arms 131, 132 which consist of generally sector-shaped blades 133, 134 affixed to shafts 136, 137. The shafts are rotatively mounted in end wall 96 and have slotted ends 136a, 137a which are accessible externally of the housing for rotation by a standard screwdriver. Thumbscrews 139, 141 are threadedly mounted in the end wall and engagable with the shafts to hold the filters in position.

The filters are movable between a normal operating position in which both filters are out of the optical path and calibration positions in which one or both of the filters are the path. The filters are independently controlled, and the optical densities (OD) of the filters are additive. Thus, for example, with neutral density filters of 0.5 OD and 1.0 OD, then a 4 point calibration of the sensor is possible, with calibration densities of 0 OD, 0.5 OD, 1.0 OD and 1.5 OD.

Figure 18:
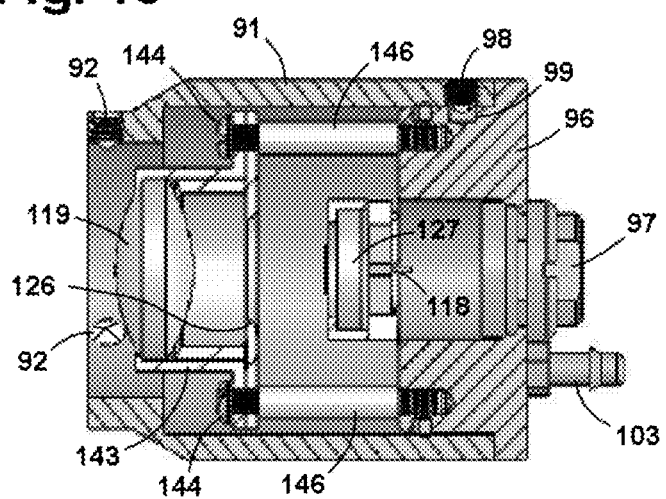
FIG. 18 is a vertical sectional view of another embodiment of an optical detector for use in the embodiment of FIG. 1.

The optical detector illustrated in FIG. 18 is similar to the detector in the embodiment of FIG. 1 without the calibration filters, and like reference numerals designate corresponding elements in the two embodiments. This detector also includes a UV silicon detector 118 and a quartz objective lens 119 which directs UV light along the optical axis and focuses it on the detector. The lens is mounted in a lens holder 143 which is attached to end wall 91 by mounting screws 144 and spacers 146. As in the embodiment of FIG. 1, an aperture 126 and a light blocking filter 127 prevent stray radiation and radiation in the visible spectrum from impinging on the detector. When used in the photocurrent mode of operation, the silicon detector exhibits best temperature stability and has linear response over 7-9 decades.

The invention has a number of important features and advantages. It provides an inline optical sensor and flowcell that can accommodate different line sizes and different optical pathlengths with a single, standardized flowcell block that will also accept different types of line connectors.

It utilizes a readily available line connection gasket that is maintained under controlled compression to provide a leak-proof seal and meets all sanitary requirements The line connection ensures proper drainage for lines of all sizes, including those with small internal diameters. The flowcell has a relatively large flow passageway which results in significantly less drop in pressure than other flowcells.

The stepped O-ring gaskets and tapered seats provide liquid-tight seals between the optical windows and the flowcell block, and interchangeable spacers allow the length of the optical path between the windows to be changed without changing the windows themselves or using windows of different lengths. In addition to providing improved sealing, the stepped O-ring gaskets also make sterilization of the flowcell easier and more effective with CIP and SIP sanitizing procedures. The tapered gasket seats provide full exposure of the liquid seals for effective CIP and SIP sterilization.

The calibration filters provide a high degree of calibration accuracy, and the vernier adjustment of the optical windows provides precise control of the optical pathlength. The optical source and detector are aligned both axially and radially of the optical axis, and the solid state UV emitter consumes less power and provides UV emissions at the desired wavelength and bandwidth without additional filtering.

The window rings and modular housings provide a flow path for the suppression of heat and condensation and, with the additional cooling provided by the air purging, allow the sensor to be used in applications with operating temperatures as high as 150° C. without exceeding the thermal ratings of sensitive components in the light source and detector, which are typically on the order of 50° C.

The invention also provides a significant decrease in the overall size and weight of the sensor and makes the sensor easier and more economical to manufacture.

It is apparent from the foregoing that a new and improved inline optical sensor and flowcell have been provided. While only certain presently preferred embodiments have been described in detail, as will be apparent to those familiar with the art, certain changes and modifications can be made without departing from the scope of the invention as defined by the following claims.

The invention claimed is:

1. An inline optical sensor, comprising a flowcell block, a flow passageway of predetermined diameter extending through the block, a plurality of adapters for connecting product lines with different internal diameters to the block, means for interchangeably attaching the adapters to the block at opposite ends of the flow passageway, monitoring ports which intersect the flow passageway and open through opposite sides of the block, optical windows disposed in the ports, a light source and an optical detector aligned with each other on an optical axis that passes through the passageway and the windows, and a plurality of spacers interchangeably positioned on opposite sides of one of the windows for establishing different optical pathlengths between the windows.

2. The sensor of claim 1 wherein each of the adapters has a bore that matches the diameter of the flow passageway at one end and the internal diameter of one of the product lines at the other and has a side wall that provides a smooth transition in diameters between the ends of the bore.

3. The sensor of claim 2 wherein the side wall is conically tapered.

4. The sensor of claim 1 including sanitary tube fitting gaskets positioned between the adapters and the block to form liquid-tight seals around the passageway in the block and the bores in the adapters.

5. The sensor of claim 4 wherein the gaskets have generally toroidal bodies received in matching grooves in facing surfaces of the adapters and the block, and annular flanges extending inwardly from the toroidal bodies, with inner faces of the flanges being aligned with the side walls of the passageway and bores.

6. The sensor of claim 5 wherein the gaskets are under controlled compression with the facing surfaces of the adapters and block in firm contact with each other.

7. The sensor of claim 1 wherein the window with the spacers is attached to the flowcell body by a mount having a cavity for receiving spacers on the outer side of the window.

8. The sensor of claim 1 wherein the spacers have widths that allow the window position to be adjusted in predetermined increments to determine the optical pathlength between the windows.

9. The sensor of claim 1 wherein the window with the spacers has a cylindrical body with a radial flange extending therefrom, and the spacers are interchangeably positioned on opposite sides of the flange.

10. The sensor of claim 9 including an annular gasket in sealing engagement with the cylindrical body of the window and the flowcell block.

11. The sensor of claim 10 wherein the gasket has an inner step of reduced diameter which is received in a conically tapered seat in the block.

12. The sensor of claim 10 including means for compressing the gasket between the radial flange and the block to adjust the pathlength between the windows.

13. The sensor of claim 12 wherein the means for compressing the gasket includes a vernier adjuster for moving the window along the optical axis.

14. The sensor of claim 1 wherein the light source and detector have modular housings which are attached to the flowcell block by means providing both radial and axial alignment of the light source and detector.

15. The sensor of claim 14 wherein the housings have cylindrical side walls disposed coaxially about cylindrical mounts affixed to the flowcell block, with O-ring seals between the housing walls and the mounts and setscrews holding the housing walls and the mounts in coaxial alignment.

16. The sensor of claim 15 wherein the setscrews are conically tapered and received in sockets of lesser diameter, with tapered walls of the screws engaging outer corners of the sockets to precisely position the housings relative to the mounts.

17. The sensor of claim 14 wherein the modular housings are thermally isolated from the flowcell block.

18. The sensor of claim 17 wherein thermal isolation is provided by O-ring seals of thermally insulative material between cylindrical side walls of the housings and mounts attached to the flowcell block and annular gaskets of thermally insulative material between end faces of the side walls and the mounts.

19. The sensor of claim 17 with means for circulating air through the housings to reduce temperature and condensation.

20. The sensor of claim 1 wherein the light source includes a solid state UV emitter.

21. The sensor of claim 1 including a filter and means for moving the filter into and out of an optical path between the source and the detector.

22. The sensor of claim 21 wherein the filter is a NIST traceable calibration standard.

23. An inline optical sensor, comprising a flowcell block, a flow passageway extending through the block, means for connecting flow lines to the block, monitoring ports which intersect the flow passageway and open through opposite sides of the block, optical windows having cylindrical bodies with radial flanges disposed in the ports, a light source and an optical detector aligned with each other on an optical axis that passes through the passageway and the windows, stepped O-ring gaskets providing liquid-tight seals between the cylindrical bodies of the windows and the flowcell block, and a plurality of spacers interchangeably positioned on opposite sides of the window flanges for establishing different optical pathlengths between the windows.

24. The sensor of claim 23 wherein the monitoring ports have outer sections with cylindrical side walls, inner sections with conically inclined side walls, and outwardly facing annular shoulders between the side walls of the two sections, and the stepped O-ring gaskets have generally annular bodies with steps of reduced outer diameter on one side thereof which are captured between and compressed by the inclined side walls of the inner sections of the ports and the cylindrical bodies of the windows.

25. The sensor of claim 24 wherein the stepped O-ring gaskets are fabricated of resilient material and have an internal diameter smaller than the cylindrical bodies of the windows.

26. The sensor of claim 23 wherein at least one of the spacers is positioned between one of the window flanges and one of the stepped O-ring gaskets.

27. The sensor of claim 23 wherein the spacers have widths that allow the window position to be adjusted in predetermined increments to determine the optical pathlength between the windows.

28. The sensor of claim 23 with vernier adjusters for moving the windows along the optical axis to adjust the pathlength between the windows.

29. An inline optical sensor, comprising a flowcell block, a flow passageway of predetermined diameter extending through the block, a plurality of adapters with tapered bores for connecting product lines having different internal diameters to the flowcell, means for interchangeably attaching the adapters to the block with the bores in the adapters in communication with the passageway in the block, monitoring ports which intersect the flow passageway and open through opposite sides of the block, optical windows disposed in the ports, a light source and an optical detector aligned with each other on an optical axis that passes through the passageway and the windows, and gaskets under controlled compression between the adapters and the block with inner faces of the gaskets aligned with side walls of the bores and the passageway.

30. The sensor of claim 29 wherein the bores have side walls that provide smooth transitions in diameter within the adapters.

31. The sensor of claim 29 wherein the gaskets are sanitary tube fitting gaskets.

32. The sensor of claim 29 wherein the gaskets have generally toroidal bodies received in matching grooves in facing surfaces of the adapters and the block, and annular flanges extending inwardly from the toroidal bodies, with inner faces of the flanges being aligned with the side walls of the passageway and bores.

33. An inline optical sensor, comprising a flowcell block, a flow passageway extending through the block, means for connecting flow lines to the block, monitoring ports which intersect the flow passageway and open through opposite sides of the block, optical windows disposed in the ports, means for adjusting the positions of the windows to provide different optical pathlengths between them, a light source and an optical detector in modular housings having cylindrical side walls disposed coaxially of cylindrical mounts on opposite sides of the block, and conical setscrews extending between the cylindrical side walls and mounts with the conical walls of the setscrews engaging sockets of lesser diameter to hold the light source and detector in both radial and axial alignment with each other.

34. The sensor of claim 33 wherein the setscrews are spaced 120 degrees apart about the axis of the side walls and the mounts.

35. The sensor of claim 33 with O-ring seals between the cylindrical side walls and the mounts cooperating with the setscrews to maintain the side walls and mounts in coaxial alignment, with gaps between the side walls and the mounts.

36. The sensor of claim 35 with thermally insulative annular gaskets between end faces of the side walls and the mounts.

37. The sensor of claim 35 with means for circulating air through the housings to reduce temperature and condensation.

38. The sensor of claim 33 wherein the housings have end walls on which the light source and the detector are mounted, with conical setscrews spaced peripherally about the side walls and sockets in the end walls in which the setscrews are received.

* * * * *